US010660616B2

(12) United States Patent
Yamamoto

(10) Patent No.: US 10,660,616 B2
(45) Date of Patent: May 26, 2020

(54) ACOUSTIC WAVE IMAGE GENERATING APPARATUS AND CONTROL METHOD THEREOF

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 436 days.

(21) Appl. No.: 15/626,529

(22) Filed: Jun. 19, 2017

(65) Prior Publication Data

US 2017/0281132 A1    Oct. 5, 2017

Related U.S. Application Data

(63) Continuation of application No. PCT/JP2016/053630, filed on Feb. 8, 2016.

(30) Foreign Application Priority Data

Mar. 10, 2015 (JP) .................................. 2015-047324

(51) Int. Cl.
*A61B 8/08* (2006.01)
*A61B 8/14* (2006.01)
*A61B 8/00* (2006.01)

(52) U.S. Cl.
CPC .......... *A61B 8/5207* (2013.01); *A61B 8/0841* (2013.01); *A61B 8/14* (2013.01); *A61B 8/4477* (2013.01); *A61B 8/463* (2013.01)

(58) Field of Classification Search
CPC ....... A61B 8/0841; A61B 8/14; A61B 8/4477; A61B 8/463; A61B 8/5207
See application file for complete search history.

(56) References Cited

U.S. PATENT DOCUMENTS

2008/0242989 A1    10/2008  Koide
2012/0078103 A1    3/2012   Tashiro et al.
(Continued)

FOREIGN PATENT DOCUMENTS

JP    2008-237788 A    10/2008
JP    2012-70816 A     4/2012
(Continued)

OTHER PUBLICATIONS

International Search Report, issued in PCT/JP2016/053630, dated Apr. 26, 2016.
(Continued)

*Primary Examiner* — Michael T Rozanski
(74) *Attorney, Agent, or Firm* — Birch, Stewart, Kolasch & Birch, LLP

(57) ABSTRACT

There are provided an acoustic wave image generating apparatus and a control method thereof for making an insertion needle clear. A first ultrasound image is generated using ultrasound echo signals obtained from a first plurality of ultrasound transducers. From the first ultrasound image, an evaluation value indicating the discontinuity of a needle is calculated for an image of an insertion needle. In a case where the calculated evaluation value is less than a threshold value, a second ultrasound image is generated using ultrasound echo signals obtained from a second plurality of ultrasound transducers whose number is larger than the first plurality. The first ultrasound image is displayed if the evaluation value is equal to or greater than the threshold value, and the second ultrasound image is displayed if the evaluation value is less than the threshold value.

10 Claims, 9 Drawing Sheets

(56) References Cited

U.S. PATENT DOCUMENTS

2012/0226164 A1 9/2012 Tashiro et al.
2015/0351717 A1* 12/2015 Tashiro ................ A61B 8/0841
600/461

FOREIGN PATENT DOCUMENTS

| JP | 2012-70837 A | 4/2012 |
| JP | 2012-192162 A | 10/2012 |

OTHER PUBLICATIONS

Written Opinion of the International Searching Authority, issued in PCT/JP2016/053630, dated Apr. 26, 2016.

* cited by examiner

ACOUSTIC WAVE IMAGE GENERATING APPARATUS AND CONTROL METHOD THEREOF

CROSS-REFERENCE TO RELATED APPLICATIONS

This application is a Continuation of PCT International Application No. PCT/JP2016/053630 filed on Feb. 8, 2016, which claims priority under 35 U.S.C. § 119(a) to Japanese Patent Application No. 2015-047324 filed Mar. 10, 2015. Each of the above application(s) is hereby expressly incorporated by reference, in its entirety, into the present application.

BACKGROUND OF THE INVENTION

1. Field of the Invention

The present invention relates to an acoustic wave image generating apparatus and a control method thereof.

2. Description of the Related Art

In anesthesia under ultrasound guidance using an ultrasound device for body surface or in aspiration biopsy cytology in an ultrasound endoscope, a procedure is performed while displaying an insertion needle on an ultrasound image. At this time, in order to make the procedure succeed, it is important for the needle to be clearly displayed on the ultrasound image. However, the needle may be difficult to see. For this reason, in a case where the needle is shifted in the thickness direction of the probe so that the needle cannot be seen, the opening of the probe is widened in the thickness direction so that the needle can be seen (JP2008-237788A). In addition, in a case where ultrasound waves cannot be received by regular reflection on the needle and accordingly the image of the needle becomes discontinuous, a receiving opening is separately set for exclusive use so that the regularly reflected components can be received, thereby receiving the regularly reflected components of the needle (JP2012-192162A).

SUMMARY OF THE INVENTION

However, if the receiving opening is simply widened, not only the amount of ultrasound echo signal for obtaining the image of the needle, which is originally required, but also the amount of noise is increased. In particular, in a convex type probe, simply widening the receiving opening is more susceptible to the influence of noise entering from an oblique direction with respect to ultrasound transducers that form the probe. If the receiving opening is too narrow, the influence of noise is reduced. However, since the amount of ultrasound echo signal for obtaining the image of the needle, which is originally required, is reduced, the image of the needle becomes discontinuous. Accordingly, it becomes difficult to see the image of the needle. In JP2008-237788A and JP2012-192162A, since the receiving opening is simply widened, it becomes easy to be influenced by noise.

It is an object of the present invention to obtain an image of a needle that is easy to see without being influenced by noise.

An acoustic wave image generating apparatus according to the present invention comprises: an acoustic wave probe in which a plurality of acoustic wave transducers are arranged in at least one direction; a transmission driving device for driving the acoustic wave transducers to transmit acoustic waves from the acoustic wave transducers to a subject; a first acoustic wave image generation device for generating a first acoustic wave image of the subject based on an acoustic wave echo from the subject using acoustic wave echo signals output from a first plurality of the acoustic wave transducers whose number is smaller than the total number of the plurality of acoustic wave transducers; an evaluation value calculation device for calculating an evaluation value of discontinuity of a needle for a needle image included in the first acoustic wave image; a second acoustic wave image generation device for generating a second acoustic wave image of the subject using acoustic wave echo signals output from a second plurality of the acoustic wave transducers, the number of which is larger than the number of first plurality of acoustic wave transducers, in a case where the evaluation value calculated by the evaluation value calculation device is less than a threshold value; and first display control device for displaying the first acoustic wave image on a display screen in a case where the evaluation value calculated by the evaluation value calculation device is equal to or greater than the threshold value and displaying the second acoustic wave image on the display screen in a case where the evaluation value calculated by the evaluation value calculation device is less than the threshold value.

The present invention also provides a control method of an acoustic wave image generating apparatus. That is, this method comprises: causing a transmission driving device to drive acoustic wave transducers of an acoustic wave probe, in which a plurality of acoustic wave transducers are arranged in at least one direction, to transmit acoustic waves from the acoustic wave transducers to a subject; causing a first acoustic wave image generation device to generate a first acoustic wave image of the subject based on an acoustic wave echo from the subject using acoustic wave echo signals output from a first plurality of the acoustic wave transducers whose number is smaller than the total number of the plurality of acoustic wave transducers; causing an evaluation value calculation device to calculate an evaluation value of discontinuity of a needle for a needle image included in the first acoustic wave image; causing a second acoustic wave image generation device to generate a second acoustic wave image of the subject using acoustic wave echo signals output from a second plurality of the acoustic wave transducers, the number of which is larger than the number of first plurality of acoustic wave transducers, in a case where the evaluation value calculated by the evaluation value calculation device is less than a threshold value; and causing a display control device to display the first acoustic wave image on a display screen in a case where the evaluation value calculated by the evaluation value calculation device is equal to or greater than the threshold value and display the second acoustic wave image on the display screen in a case where the evaluation value calculated by the evaluation value calculation device is less than the threshold value.

The acoustic wave image generating apparatus may further comprise a needle image extraction device for extracting a needle image from the first acoustic wave image. In this case, the evaluation value calculation device may calculate an evaluation value of discontinuity of the needle for the needle image extracted by the needle image extraction device, for example.

The acoustic wave image generating apparatus may further comprise a first control device for making the transmission driving device, the first acoustic wave image generation device, and the needle image extraction device repeat transmission of acoustic waves based on driving of the transmission driving device, generation of the first acoustic wave image by the first acoustic wave image generation device, and extraction of a needle image by the needle image extraction device in a case where the needle image is not extracted by the needle image extraction device.

The first control device stops the transmission of acoustic waves based on driving of the transmission driving device, generation of the first acoustic wave image by the first acoustic wave image generation device, and the extraction of a needle image by the needle image extraction device, for example, in a case where the number of repetitions reaches the first number of times or in a case where a stop command is given (for example, in a case where a temporary stop command, an examination end command, or the like from a user is given).

The acoustic wave image generating apparatus may further comprise a second display control device for displaying the first acoustic wave image on the display screen. In this case, for example, in a case where the first acoustic wave image is displayed by the second display control device and an evaluation value calculation command for starting calculation of the evaluation value by the evaluation value calculation device is input, the evaluation value calculation device may calculate the evaluation value of the discontinuity of the needle for the needle image included in the first acoustic wave image. In addition, for example, the first display control device displays the first acoustic wave image on the display screen in a case where the evaluation value is equal to or greater than the threshold value, and displays the second acoustic wave image on the display screen in a case where the evaluation value calculated by the evaluation value calculation device is less than the threshold value.

The acoustic wave image generating apparatus may further comprise a second control device for repeating processing for increasing the number of second plurality of acoustic wave transducers by a predetermined number, processing for generating a second acoustic wave image of the subject using acoustic wave echo signals output from the second plurality of acoustic wave transducers increased by the predetermined number, and processing for calculating an evaluation value of discontinuity of the needle using the generated second acoustic wave image, until the evaluation value becomes equal to or greater than the threshold value in a case where the evaluation value calculated by the evaluation value calculation device is less than the threshold value.

For example, in a case where the number of repetitions reaches the second number of times, the second control device stops processing in the evaluation value calculation device and processing in the second acoustic wave image generation device.

For example, the first plurality of acoustic wave transducers and the second plurality of acoustic wave transducers overlap each other, and the acoustic wave transducer present at a center of the first plurality of acoustic wave transducers and the acoustic wave transducer present at a center of the second plurality of acoustic wave transducers are the same.

Both the first plurality and the second plurality may be odd numbers.

According to the present invention, the first acoustic wave image generation device generates the acoustic wave image (first acoustic wave image) of the subject using the acoustic wave echo signals output from the first plurality of acoustic wave transducers among the acoustic wave transducers included in the acoustic wave probe. The evaluation value of the discontinuity of the needle is calculated for the needle image included in the generated acoustic wave image. In a case where the evaluation value is less than the threshold value, the second acoustic wave image generation device generates the acoustic wave image (second acoustic wave image) of the subject using the acoustic wave echo signals output from the second plurality of acoustic wave transducers whose number is larger than the number of first plurality of acoustic wave transducers. In a case where the evaluation value is less than the threshold value, the acoustic wave image generated by the second acoustic wave image generation device is displayed. In a case where the evaluation value is equal to or greater than the threshold value, the acoustic wave image generated by the first acoustic wave image generation device is displayed. Since the acoustic wave image generated by the second acoustic wave image generation device is generated using the acoustic wave echo signals output from the second plurality of acoustic wave transducers whose number is larger than the number of first plurality of acoustic wave transducers, a needle image that is not discontinuous is projected. In a case where the evaluation value is equal to or greater than the threshold value, since the acoustic wave image generated using the acoustic wave echo signals output from the first plurality of acoustic wave transducers whose number is smaller than the number of second plurality of acoustic wave transducers is displayed, an acoustic wave image with little influence of noise is displayed. It is possible to display an acoustic wave image with little influence of noise in a case where the image of the needle is not discontinuous, and it is possible to display the image of the needle more clearly only when necessary as in the case where the image of the needle is discontinuous.

DESCRIPTION OF THE PREFERRED EMBODIMENTS

Figure 1:
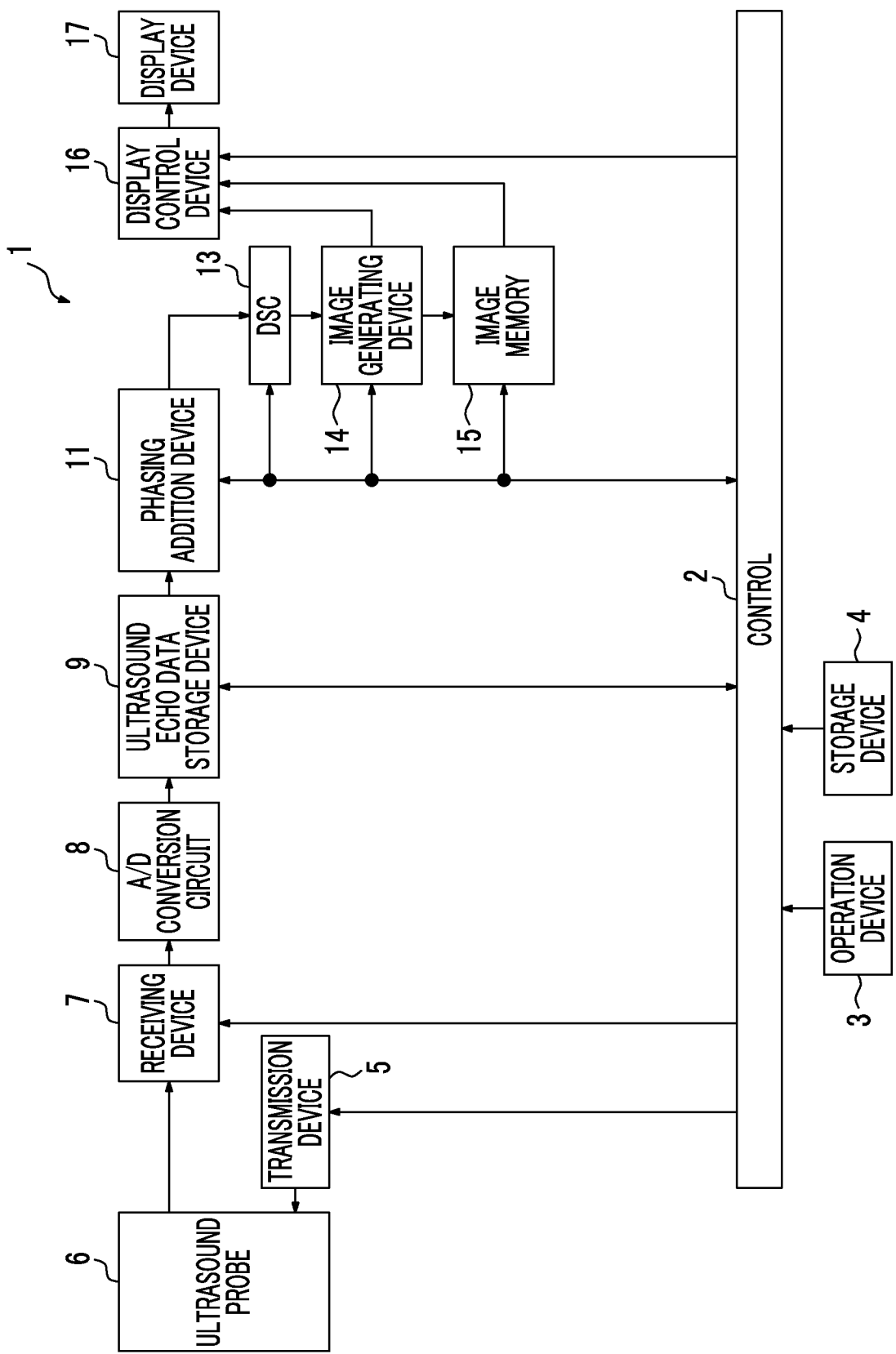
FIG. 1 is a block diagram showing the electrical configuration of an ultrasound diagnostic apparatus.

FIG. 1 shows an embodiment of the present invention, and is a block diagram showing the electrical configuration of an ultrasound diagnostic apparatus 1 (acoustic wave image generating apparatus).

In the present embodiment, an ultrasound wave is used as an acoustic wave. However, as long as an appropriate frequency is selected according to an object to be examined, measurement conditions, and the like, an acoustic wave having an audible frequency may be used without being limited to the ultrasound wave.

The overall operation of an ultrasound diagnostic apparatus 1 is controlled by a control device 2.

An operation device 3, which is operated by a doctor or the like who operates the ultrasound diagnostic apparatus 1, and a storage device 4, in which predetermined data and the like are stored, are connected to the control device 2.

An ultrasound probe 6 (acoustic wave probe) is included in the ultrasound diagnostic apparatus 1. A plurality of ultrasound transducers (acoustic wave transducers) are included in the ultrasound probe 6.

A control signal output from the control device 2 is supplied to a transmission device 5. Then, an electrical pulse is supplied to each ultrasound transducer of the ultrasound probe 6 from the transmission device 5. The ultrasound transducer is driven by the transmission device 5 (a transmission driving device). The electrical pulse is converted into an ultrasound pulse (ultrasound wave) by the ultrasound transducer, the ultrasound pulse propagates through the body of a subject, and the ultrasound echo returns to the ultrasound probe 6.

The ultrasound echo is converted into an electrical signal (ultrasound echo signal) by the ultrasound transducer. The ultrasound echo signal is supplied to a receiving device 7. The ultrasound echo signal is amplified by the receiving device 7, and is converted into digital ultrasound echo data by an analog/digital conversion circuit 8. The ultrasound echo data is supplied to an ultrasound echo data storage device 9 so as to be temporarily stored therein.

The ultrasound echo data is supplied to a phasing addition device 11. In the phasing addition device 11, phasing addition (processing for adding phases after aligning the phases of ultrasound echo data generated due to a difference between the positions of ultrasound transducers included in the ultrasound probe 6 or the like) is performed. By performing the phasing addition, the S/N ratio is improved.

The ultrasound echo data after the phasing addition in the phasing addition device 11 is input to a digital scan converter (DSC) 13. The DSC 13 performs raster conversion into image data according to the normal scan method of television signals. The image data output from the DSC 13 is subjected to image processing, such as gradation processing, by an image generating device 14. An ultrasound image (B-mode image) showing the brightness of the subject is generated from the superimposed signal. The image data output from the image generating device 14 is supplied to a display control device 16, and an ultrasound image is displayed on the display screen of a display device 17. The image data output from the image generating device 14 is also supplied to an image memory 15, and the image data indicating an ultrasound image is stored in the image memory 15. By supplying the image data stored in the image memory 15 to the display control device 16, the ultrasound image is displayed on the display screen of the display device 17.

The ultrasound diagnostic apparatus 1 according to the present embodiment is used by a user, such as a doctor, to insert an insertion needle into a subject, take cells or the like in the subject, and perform diagnosis or the like.

Figure 2:
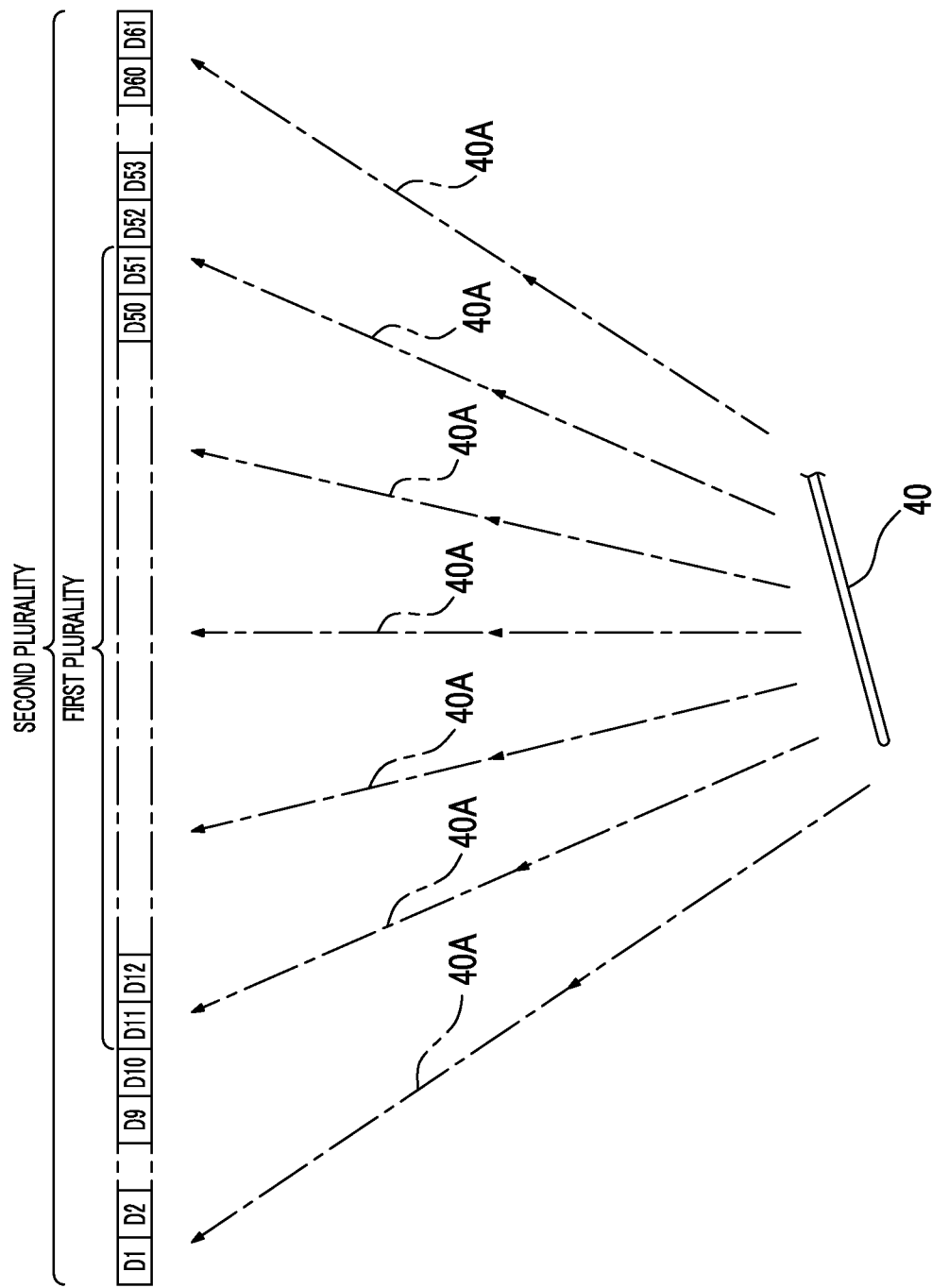
FIG. 2 shows an ultrasound echo from an insertion needle.

FIG. 2 shows a state in which an insertion needle 40 has been inserted into a subject.

As described above, 120 ultrasound transducers are included in the ultrasound probe 6. However, the number of ultrasound transducers may be more than 120, or may be less than 120. In FIG. 2, among the 120 ultrasound transducers, ultrasound transducers D1 to D61 that are simultaneously used for one transmission and reception of ultrasound waves are shown. However, the number of ultrasound transducers that are simultaneously used for one transmission and reception of ultrasound waves may be less than 61 or may be more than 61. In addition, the ultrasound transducers D1 to D61 shown in FIG. 2 are linearly arranged in one direction. However, the ultrasound transducers D1 to D61 may be arranged in one direction in an arc shape as in a convex ultrasound probe.

In the present embodiment, as will be described later, the number of ultrasound transducers driven around the scanning line (line to be scanned) is changed. However, in a case where there is no such a change, a total of 61 ultrasound transducers including 30 ultrasound transducers on each of the left and right sides around the scanning line (30 on each of the left and right sides and one in a portion corresponding to the scanning line) are driven. However, in the scanning line in an end portion of the ultrasound image, a smaller number of ultrasound transducers than 61 ultrasound transducers are driven. For example, the ultrasound transducers D1 to D31 are driven in the scanning line of the scanning line No 1, and the ultrasound transducers D1 to D32 are driven in the scanning line of the scanning line No 2. Hereinafter, the number of ultrasound transducers to be driven increases each time the scanning line No increases, and the ultrasound transducers D1 to D61 are driven in the scanning line of the scanning line No 31. D2 to D62 are driven in the scanning line of the scanning line No 32, and D90 to D120 are driven in the scanning line of the scanning line No 120 in the end portion of the ultrasound image.

FIG. 2 shows the ultrasound transducers D1 to D61 among 120 ultrasound transducers driven in this manner. Although the ultrasound transducers D62 to D120 are present in the ultrasound probe 6, the ultrasound transducers D62 to D120 are omitted in FIG. 2. In a case where there is no change in the number of ultrasound transducers to be driven, the ultrasound transducers D1 to D61 shown in FIG. 2 are driven in the scanning line of the scanning line No 31.

In the case of the scanning line of the scanning line No 31, the ultrasound transducers D1 to D61 are driven by the transmission device 5 (a transmission driving device) in a state in which the insertion needle 40 has been inserted into the subject, so that ultrasound waves are transmitted from the ultrasound transducers D1 to D61. Then, ultrasound waves are reflected by the insertion needle 40 inserted into the subject, and an ultrasound echo 40A is input to each of the ultrasound transducers D1 to D61. An ultrasound signal is output from each of the ultrasound transducers D1 to D61. These operations are also performed in each scanning line other than the scanning line No 31. As described above, using the ultrasound signal obtained by driving the ultrasound transducer in each scanning line, an ultrasound image including the insertion needle 40 is displayed on the display screen of the display device 17.

In the present embodiment, first, an ultrasound image (first ultrasound image) of the subject is generated as described above using ultrasound echo signals output from a first plurality (41) of ultrasound transducers D11 to D51 smaller than 61 (maximum number of receiving openings) ultrasound transducers, which are driven at one time in transmission and reception of ultrasound waves, among a plurality (120) of ultrasound transducers arranged in the ultrasound probe 6. When an ultrasound image is generated using ultrasound echo signals obtained from 61 (maximum number of receiving openings) ultrasound transducers, the ultrasound transducers also receive a noise signal, and the generated ultrasound image is also influenced by noise. Therefore, in order to eliminate the influence of noise as much as possible, the first ultrasound image is generated using the first plurality (41) of ultrasound transducers D11 to D51, instead of generating the first ultrasound image using ultrasound echo signals obtained from all of the 61 (maximum number of receiving openings) ultrasound transducers. Taking the scanning line No 31 as an example, from FIG. 2, the maximum number of receiving openings 61 indicates the ultrasound transducers D1 to D61, and the first plurality (41) of ultrasound transducers indicate D11 to D51. The number of the first plurality is not limited to 41, and may be smaller than 61 that is the maximum number of receiving openings. In the first ultrasound image obtained as described above, evaluation of the discontinuity of the needle is performed for the insertion needle 40. As a result of the evaluation, when it is determined that the image of the insertion needle 40 is difficult to see, an ultrasound image (second ultrasound image) of the subject is generated using ultrasound echo signals output from a second plurality (61 in the present embodiment) of ultrasound transducers D1 to D61 whose number is larger than the number of the first plurality and is equal to or less than 61 that is the maximum number of receiving openings. Since the second ultrasound image is generated using ultrasound echo signals obtained from a number of ultrasound transducers, the insertion needle 40 is easy to see.

It is preferable that the first plurality of ultrasound transducers D11 to D51 and the second plurality of ultrasound transducers D1 to D61 overlap each other. An ultrasound transducer present at the center of the first plurality of ultrasound transducers D11 to D51 and an ultrasound transducer present at the center of the second plurality of ultrasound transducers D1 to D61 may be the same. The sensitivity of the ultrasound echo signal received by each ultrasound transducer has directivity, and the sensitivity of the ultrasound echo signal in the case of vertical incidence is higher than that in the case of oblique incidence. The ultrasound echo 40A is obliquely incident on the ultrasound transducers located at the ends of the receiving openings. Accordingly, the ratio of a noise component in the ultrasound echo signal output from these ultrasound transducers is larger than that in the ultrasound echo signal output from the ultrasound transducer located at the center. Therefore, it is preferable that the ultrasound transducer located at the center of the first plurality of ultrasound transducers and the ultrasound transducer located at the center of the second plurality of ultrasound transducers are the same, and it is preferable that the scanning lines are the same. The first plurality and the second plurality defined as described above are not limited to odd numbers but may be even numbers. In this case, since there is no central ultrasound transducer, the middle of two ultrasound transducers near the center may be defined as the center.

The example shown in FIG. 2 is for the scanning line No 31. Similarly for scanning lines other than the scanning line No 31, it is needless to say that the driving of the first plurality of ultrasound transducers and the driving of the second plurality of ultrasound transducers are switched for each scanning line.

Figure 3:
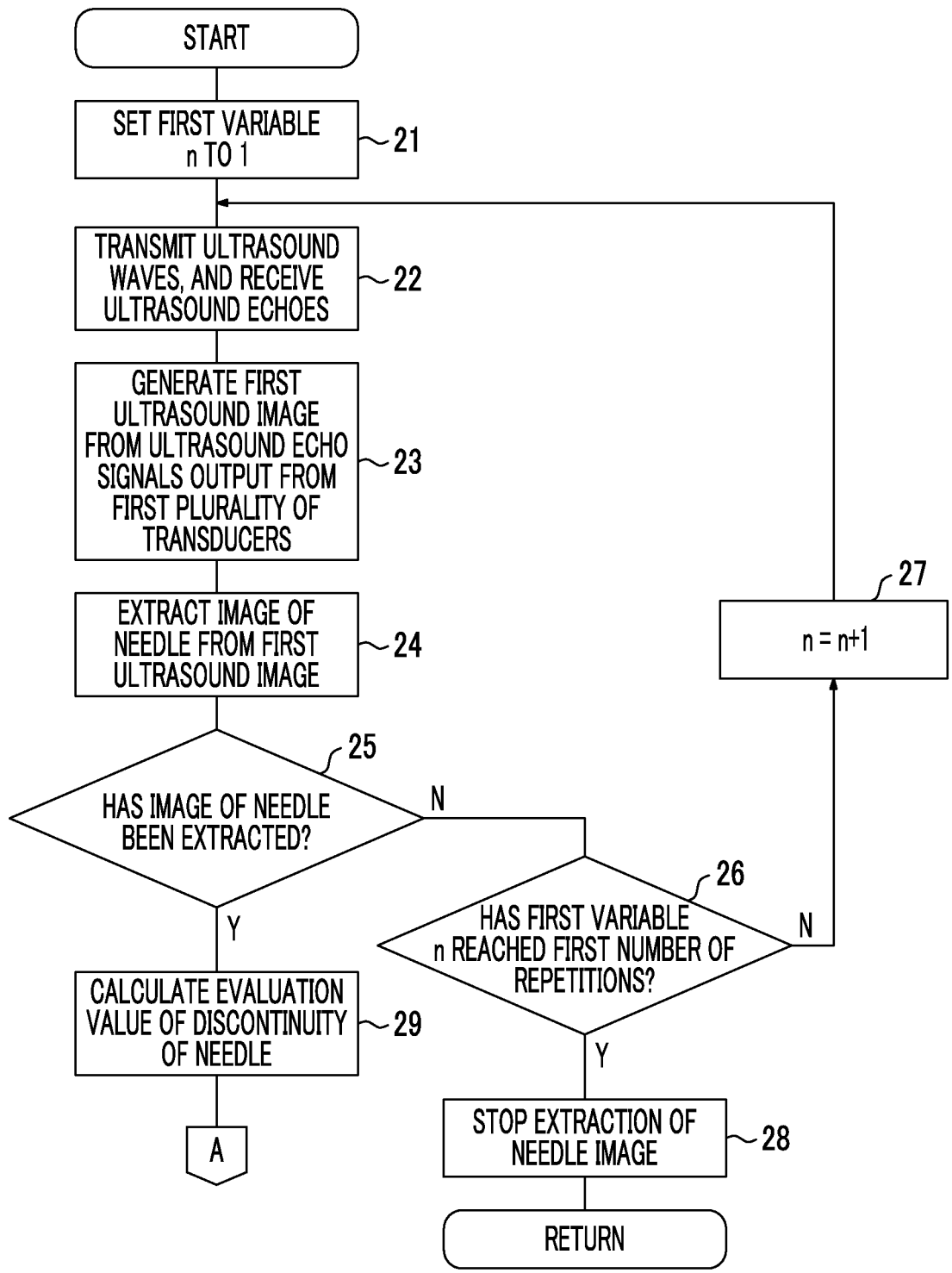
FIG. 3 is a flowchart showing the procedure of the processing of the ultrasound diagnostic apparatus.
Figure 4:
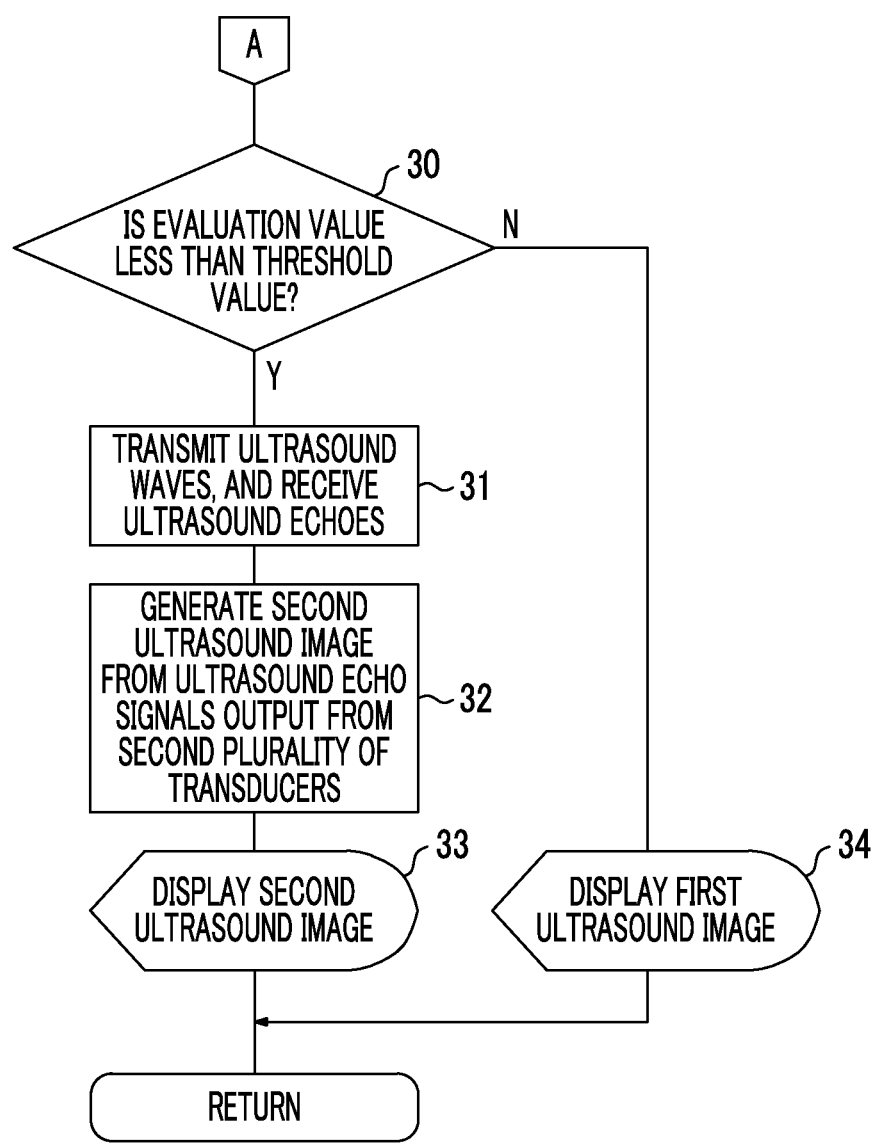
FIG. 4 is a flowchart showing the procedure of the processing of the ultrasound diagnostic apparatus.

FIGS. 3 and 4 are flowcharts showing the procedure of the processing of the ultrasound diagnostic apparatus 1.

As described above, the evaluation of the insertion needle 40 included in the first ultrasound image is performed. In the present embodiment, however, an image of the insertion needle 40 is extracted from the first ultrasound image, and evaluation of the discontinuity of the insertion needle 40 is performed for the extracted image of the insertion needle 40. At that time, in a case where it is not possible to extract the image of the insertion needle 40, the extraction is repeated until the number of times of extraction becomes the first number of repetitions (first number of times). A first variable n (the number of repetitions) for determining whether or not the number of times of extraction has reached the first number of repetitions is set to 1 (step 21). Even if the number of times of extraction does not reach the first number of repetitions, the user gives a stop command, such as a temporary stop command or an examination end command, using the operation device 3, so that the generation of an ultrasound image and the extraction of an image of a needle are stopped as described later.

Then, ultrasound waves are transmitted from the ultrasound transducers D1 to D120 of the ultrasound probe 6 at each scanning line, and the ultrasound echo 40A from the insertion needle 40 is received by the ultrasound transducers D1 to D120 at each scanning line (step 22). As described above, ultrasound transducers to be driven are different for each scanning line. In each scanning line, using the ultrasound echo signals output from the first plurality of ultrasound transducers (for example, the ultrasound transducers D11 to D51 in the case of the scanning line No 31) as described above among the maximum number of receiving openings 61, the ultrasound image (first ultrasound image) of the subject is generated by the phasing addition device 11, the DSC 13, and the image generating device 14 (a first acoustic wave image generation device) (step 23).

Then, the image of the insertion needle 40 is extracted from the generated first ultrasound image of the subject by the control device 2 (a needle image extraction device) (step 24). Examples of the extraction of the image of the insertion needle 40 include extraction of a linear component using Hough transformation or the like, extraction using a fluctuation in the ultrasound echo signal obtained from the ultrasound echo 40A from the insertion needle 40 that is inserted to move, extraction based on the direct designation of the image of the insertion needle 40 from a doctor operating the ultrasound diagnostic apparatus 1, and the like. In addition, the position of the insertion needle 40 can be specified from the actual insertion angle of the insertion needle 40 using an angle sensor, a guide of the insertion needle 40, or the like. In a case where a magnetic sensor or the like is attached to the distal end of the insertion needle 40, the position of the insertion needle 40 can be specified by detecting the magnetic sensor. However, since it is only necessary to calculate an evaluation value indicating the discontinuity of the needle as described later, the image of the insertion needle 40 does not necessarily need to be extracted.

If the image of the insertion needle 40 is not extracted by the control device 2 (NO in step 25), the control device 2 checks whether or not the first variable n has reached the first number of repetitions (step 26). If the first variable n does not reach the first number of repetitions (NO in step 26), the first variable n is incremented by the control device 2 (step 27), so that the processing from step 22 is repeated (transmission of acoustic waves based on the transmission driving device, generation of an acoustic wave image by the first acoustic wave image generation device, and extraction of a needle image by the needle image extraction device are repeated by the transmission driving device, the first acoustic wave image generation device, and the needle image extraction device). If the image of the insertion needle 40 is not extracted from the first ultrasound image even if the first variable n reaches the first number of repetitions (YES in step 26), the processing of extracting the image of the insertion needle 40 is stopped (step 28) (in a case where the number of repetitions has reached the first number, transmission of acoustic waves based on the driving of the transmission driving device, generation of an acoustic wave image by the first acoustic wave image generation device, and extraction of a needle image by the needle image extraction device are stopped).

If the image of the insertion needle 40 is extracted from the first ultrasound image (YES in step 25), an evaluation value of the discontinuity of the insertion needle 40 is calculated by the control device 2 (an evaluation value calculation device) (step 29), and it is determined whether or not the calculated evaluation value is less than a threshold value (step 30). As an example of the evaluation value of the discontinuity of the insertion needle 40, for example, a standard deviation (this standard deviation is an example of the evaluation value) in a direction along the insertion needle 40 is taken in the extracted image of the insertion needle 40. If the standard deviation is less than a reference value (threshold value), it is determined that the evaluation value is less than the threshold value. If the standard deviation is larger than the reference value, it is determined that the evaluation value is equal to or greater than the threshold value. As another example of the evaluation value of the discontinuity of the insertion needle 40, if an average (this average is an example of the evaluation value) of the amplitude levels of the ultrasound echo data for each ultrasound transducer obtained from the first plurality of ultrasound transducers (for example, the ultrasound transducers D11 to D51 in the case of the scanning line No 31) is less than a predetermined threshold value, it is determined that the calculated evaluation value is less than the threshold value. If the average is equal to or greater than the predetermined threshold value, it is determined that the calculated evaluation value is equal to or greater than the threshold value. As still another example of the evaluation value of the discontinuity of the insertion needle 40, if a correlation value (this correlation value is another example of the evaluation value) between the ideal image of the insertion needle and the extracted image of the insertion needle 40 is calculated by the control device 2. If the calculated correlation value is less than a threshold value, it is determined that the calculated evaluation value is less than the threshold value. If the calculated correlation value is equal to or greater than the threshold value, it is determined that the calculated evaluation value is equal to or greater than the threshold value. For example, assuming that the data of the ideal image of the insertion needle is St(t), the data of the extracted image of the insertion needle 40 is Si(t), and i is the number of pixels of an image, a correlation value Ri is obtained as $Ri=[\Sigma\{St(t) \times Si(t)\}]/[\sqrt{\Sigma\{St(t)\}^2} \times \sqrt{\Sigma\{Si(t)\}^2}]$. In any case, when the control device 2 determines that the evaluation value is less than the threshold value (YES in step 30), the control device 2 determines that the insertion needle 40 is discontinuous. Data indicating the threshold value is stored in, for example, the storage device 4, and it is needless to say that the data is read by the control device 2 in the case of comparison with the evaluation value.

Figure 5:
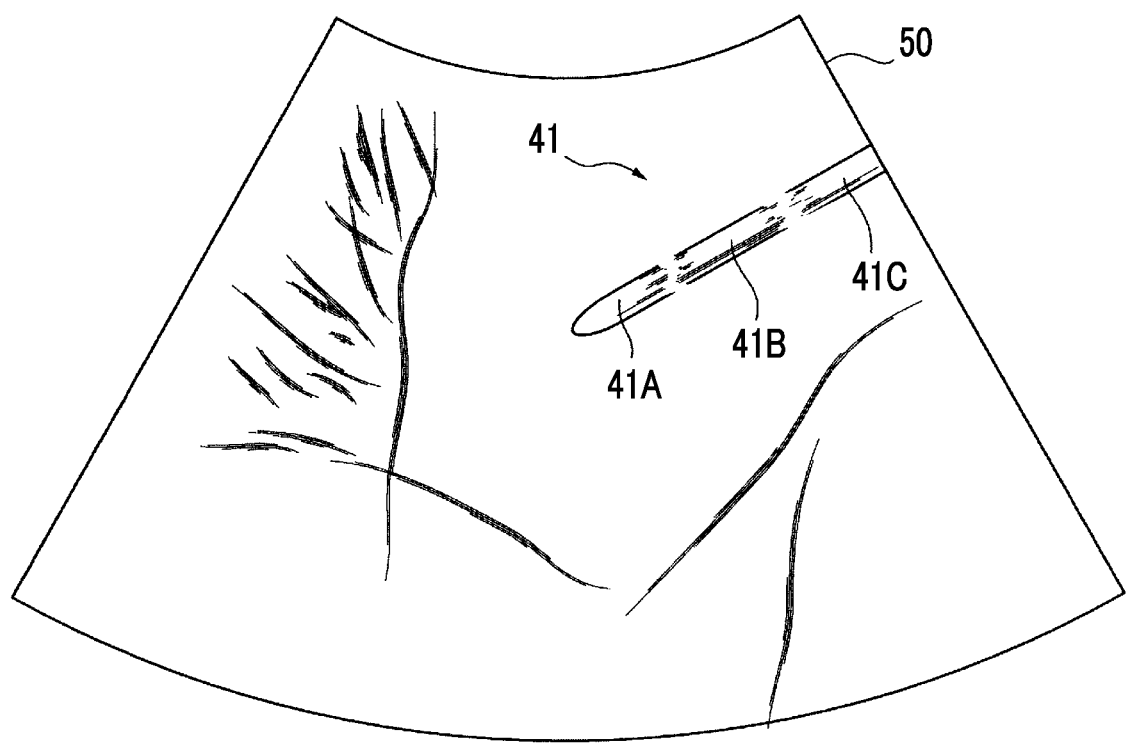
FIG. 5 is an example of an ultrasound image.

FIG. 5 is a first ultrasound image 50 generated based on the ultrasound echo signals output from the first plurality of ultrasound transducers (for example, the ultrasound transducers D11 to D51 in the case of the scanning line No 31), the number of which is the number of receiving openings.

An image 41 of the insertion needle 40 is included in the first ultrasound image 50. The image 41 of the insertion needle 40 is divided into three portions of a first needle image portion 41A, a second needle image portion 41B, and a third needle image portion 41C. That is, the image 41 of the insertion needle 40 is discontinuous. When such an image 41 is extracted and the evaluation value is calculated as described above, the calculated evaluation value becomes less than the threshold value. Accordingly, the control device 2 determines that the image of the insertion needle 40 is discontinuous.

Figure 6:
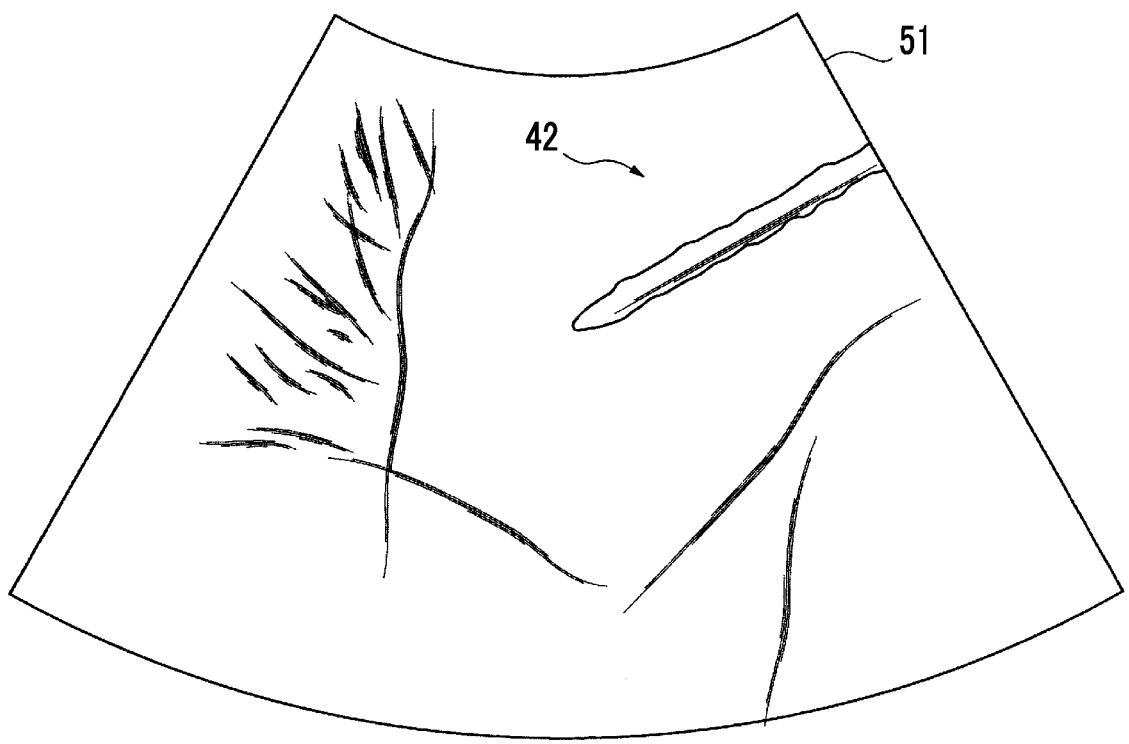
FIG. 6 is an example of an ultrasound image.

FIG. 6 is a first ultrasound image 51 generated based on the ultrasound echo signals output from the first plurality of ultrasound transducers (for example, the ultrasound transducers D11 to D51 in the case of the scanning line No 31), the number of which is the number of receiving openings.

In an image 42 of the insertion needle 40 included in the first ultrasound image 51 shown in FIG. 6, the edge of the insertion needle 40 is not a straight line but a curve. Even for such an image 42, the evaluation value that is calculated as described above is less than the threshold value. Thus, even if the image 42 of the insertion needle 40 does not show the insertion needle 40 that is completely discontinuous, the evaluation value is less than the threshold value. However, as shown in FIG. 5, if the image 41 of the insertion needle 40 is not completely discontinuous, the evaluation value may not be less than the threshold value.

Figure 7:
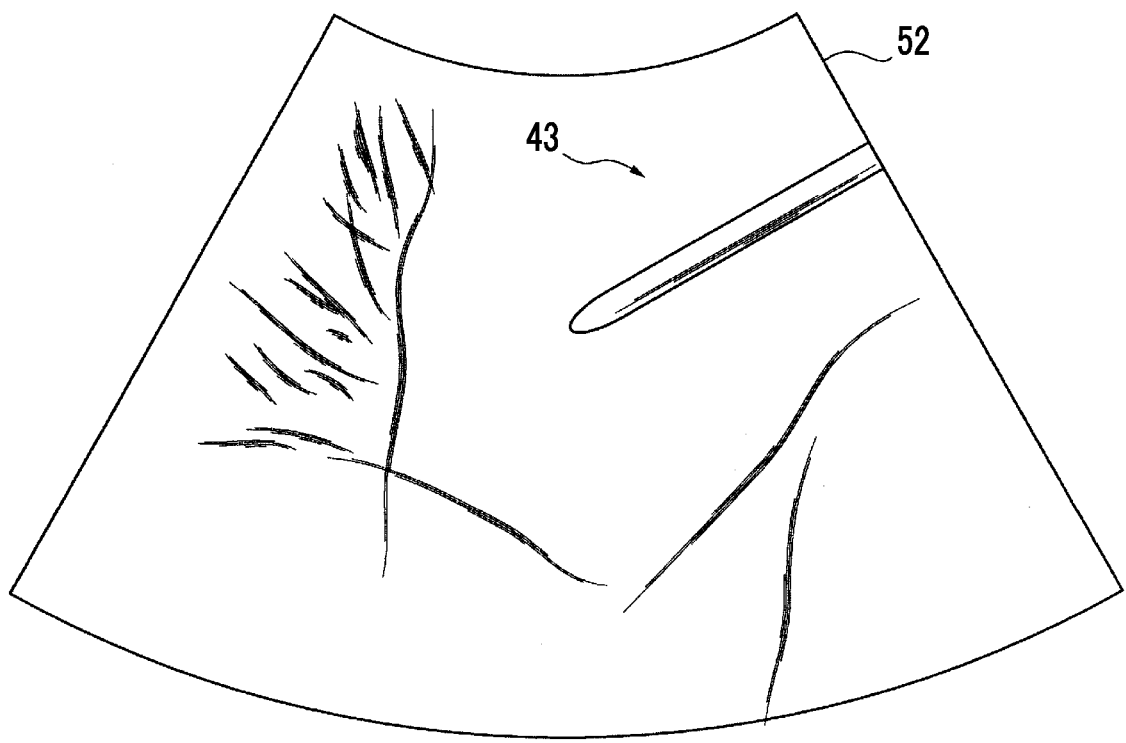
FIG. 7 is an example of an ultrasound image.

FIG. 7 is a first ultrasound image 52 generated based on the ultrasound echo signals output from the first plurality of ultrasound transducers (for example, the ultrasound transducers D11 to D51 in the case of the scanning line No 31), the number of which is the number of receiving openings.

In an image 43 of the insertion needle 40 included in the first ultrasound image 52 shown in FIG. 7, the insertion needle 40 is not discontinuous, and the edge is not a curve but a straight line. Thus, when an evaluation value is calculated for the image 43 in which the insertion needle 40 is not discontinuous, the evaluation value is equal to or greater than the threshold value.

Referring to FIG. 4, if the evaluation value is equal to or greater than the threshold value (NO in step 30), it is considered that, in the image of the insertion needle 40, the insertion needle 40 is not discontinuous as shown in FIG. 7. Accordingly, it is possible to perform diagnosis while observing the insertion needle 40. For this reason, the generated first ultrasound image (first ultrasound image 52) is displayed on the display screen of the display device 17 by the control device 2 and the display control device 16 (a first display control device). The doctor performs diagnosis by operating the insertion needle 40 while observing the first ultrasound image.

If the evaluation value is less than the threshold value (YES in step 30), ultrasound waves are transmitted from the second plurality of ultrasound transducers, among the ultrasound transducers of the ultrasound probe 6, for each scanning line (ultrasound waves are transmitted from the ultrasound transducers Dl to D61 in the case of the scanning line No 31), and the ultrasound echo 40A from the insertion needle 40 is received by 61 ultrasound transducers that are the maximum number of receiving openings (step 31) (the ultrasound echo 40A is received by the ultrasound transducers D1 to D61 in the case of the scanning line No 31). Then, the second ultrasound image is generated by the phasing addition device 11, the DSC 13, and the image generating device 14 (a second acoustic wave image generation device) as described above using the ultrasound echo signals output from the second plurality of ultrasound transducers (step 32). The generated second ultrasound image is displayed on the display screen of the display device 17 by the control device 2 and the display control device 16 (a first display control device) (step 33). Since the second ultrasound image is generated using the ultrasound echo signals output from the larger number of second ultrasound transducers than the number of first plurality of ultrasound transducers used for generating the first ultrasound image, the image of the insertion needle 40 is not discontinuous like the image 43 shown in FIG. 7.

Figure 8:
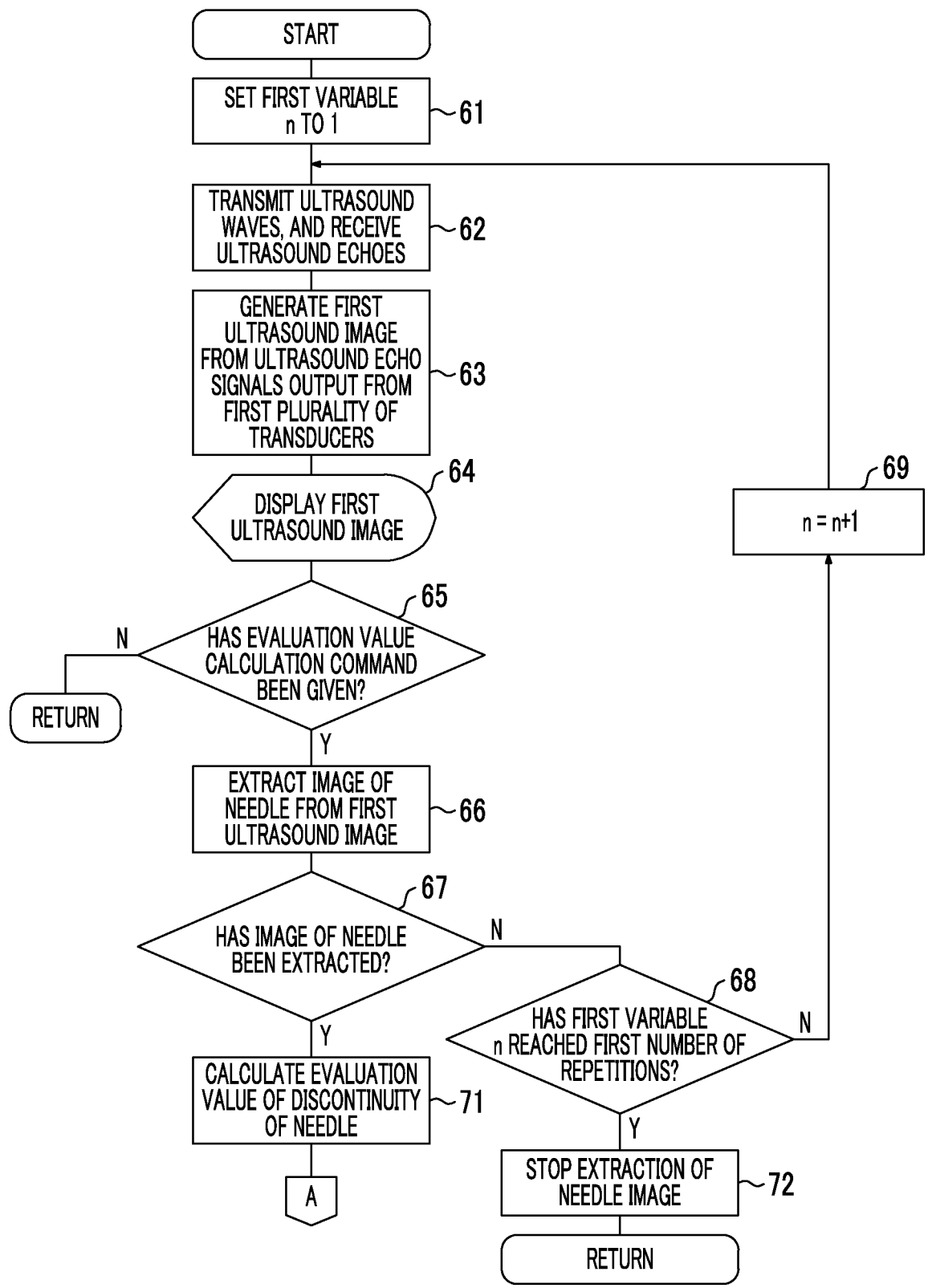
FIG. 8 is a block diagram showing the electrical configuration of an ultrasound diagnostic apparatus.
Figure 9:
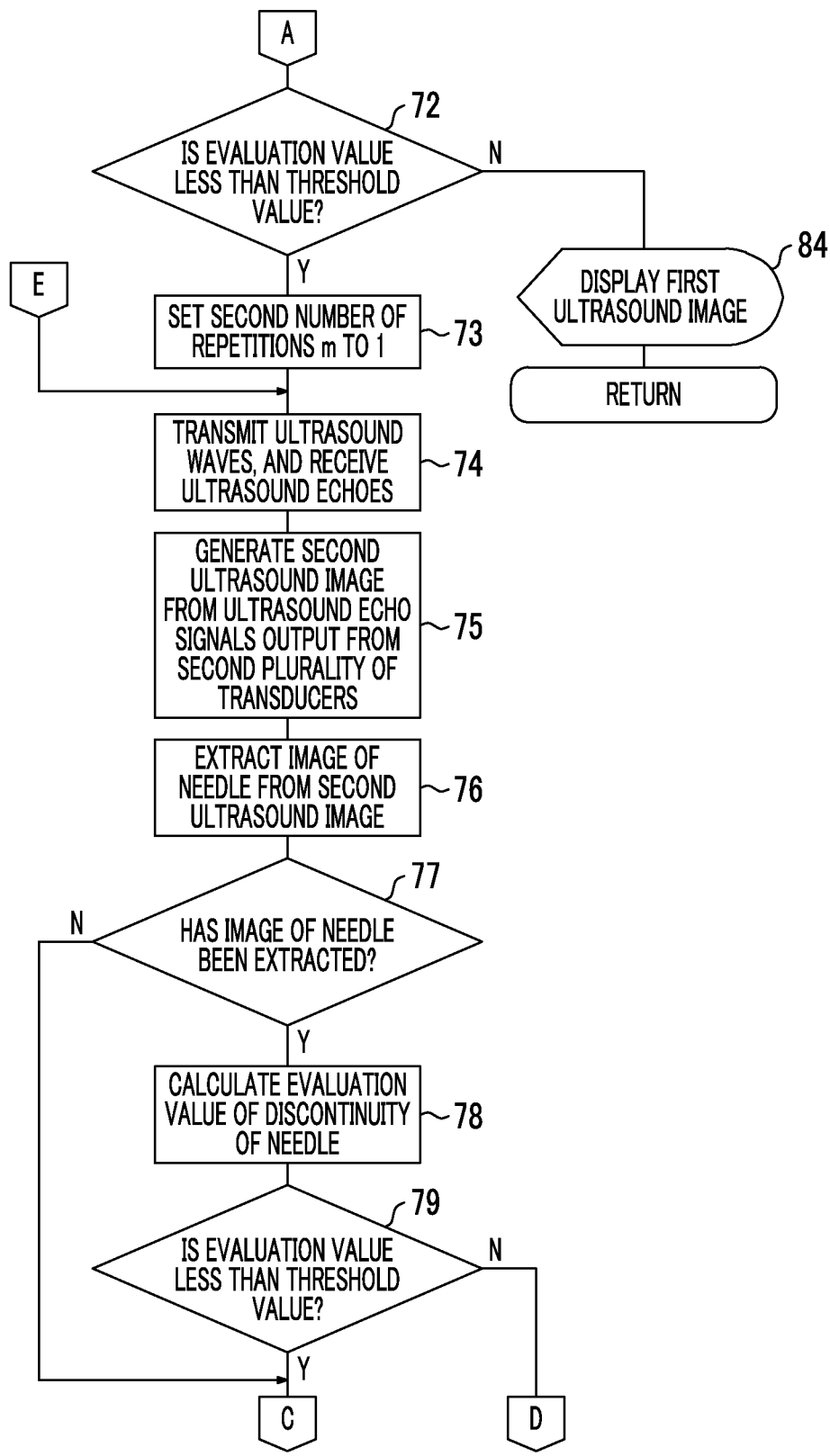
FIG. 9 is a flowchart showing the procedure of the processing of the ultrasound diagnostic apparatus.
Figure 10:
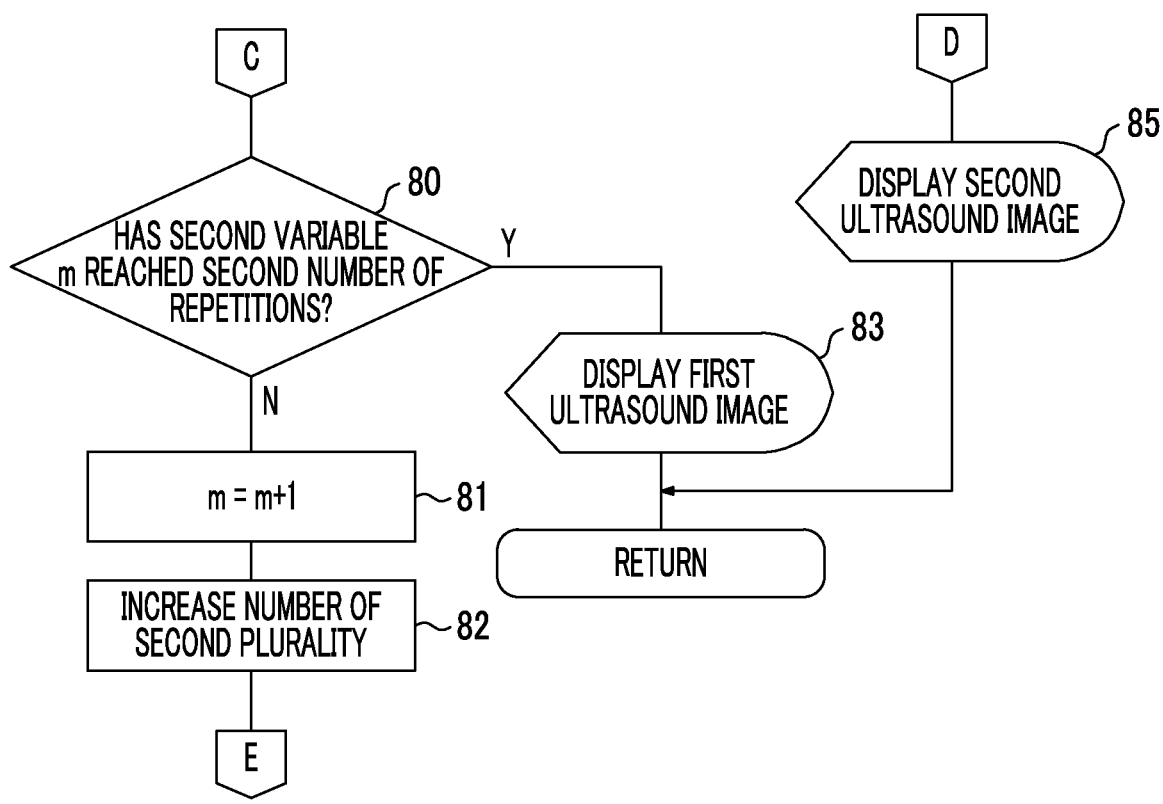
FIG. 10 is a flowchart showing the procedure of the processing of the ultrasound diagnostic apparatus.

FIGS. 8 to 10 show another embodiment, and are flowcharts showing the procedure of the processing of the ultrasound diagnostic apparatus 1.

As described above, the first variable n is set to 1 (step 61), transmission of ultrasound waves and reception of the ultrasound echo 40A are performed (step 62), and a first ultrasound image is generated using ultrasound echo signals output from the first plurality of ultrasound transducers (for example, D11 to D51 in the case of the scanning line No 31) for each scanning line (step 63). In the present embodiment, when the first ultrasound image is generated, the generated first ultrasound image is displayed on the display screen of the display device 17 by the control device 2 and the display control device 16 (a second display control device) (step 64). The doctor sees the image of the insertion needle 40 included in the first ultrasound image displayed on the display screen, and inputs an evaluation value calculation command to the ultrasound diagnostic apparatus 1 using the operation device 3 in a case where the doctor desires to see a clearer image of the insertion needle 40 (YES in step 65). The evaluation value calculation command has a function of starting the calculation of the evaluation value of the discontinuity of the needle by the evaluation value calculation device, and has, for example, an aspect like an input signal. Then, as described above, the image of the insertion needle 40 is extracted from the generated first ultrasound image (step 66). In a case where the image of the insertion needle 40 is not extracted (NO in step 67), if the first variable n does not reach the first number of repetitions (NO in step 68), the first variable n is incremented (step 69) and the processing of steps 62 to 66 is repeated. If the first variable n reaches the first number of repetitions (YES in step 68), extraction of the needle image is stopped (step 70).

As described above, when the image of the insertion needle 40 is extracted from the first ultrasound image (YES in step 67), an evaluation value of the discontinuity of the insertion needle 40 is calculated (step 71), and it is determined whether or not the evaluation value is less than the threshold value (step 72). If the evaluation value is equal to or greater than the threshold value (NO in step 72), the generated first ultrasound image is displayed on the display screen of the display device 17 (step 84).

If the evaluation value is less than the threshold value (YES in step 72), a second variable m is set to 1 by the control device 2 (step 73). In the same manner as described above, ultrasound waves are transmitted for each scanning line, and the ultrasound echo 40A from the insertion needle 40 is received in each scanning line (step 74). A second ultrasound image is generated using the ultrasound echo signals output from the second plurality of ultrasound transducers (for example, D11 to D51 in the case of the scanning line No 31) (step 75). The image of the insertion needle 40 is extracted from the generated second ultrasound image (step 76).

If the image of the insertion needle 40 is extracted from the second ultrasound image (YES in step 77), an evaluation value of the discontinuity of the insertion needle is calculated (step 78). If the calculated evaluation value is equal to or greater than the threshold value (NO in step 79), the generated second ultrasound image is displayed on the display screen of the display device 17 (step 85). In a case where the calculated evaluation value is less than the threshold value (YES in step 79) or the image of the insertion needle 40 is not extracted from the second ultrasound image (NO in step 77), it is checked whether or not the second variable m has reached the second number of repetitions (step 80).

If the second variable in reaches the second number of repetitions (YES in step 80), it is considered that the second ultrasound image does not include a clear image of the insertion needle 40, and the first ultrasound image is displayed on the display device 17 (step 83). In this case, error processing may be performed, and display of the first ultrasound image may not be performed. In a case where the image of the insertion needle 40 is extracted from the second ultrasound image, the second ultrasound image may be displayed even if the evaluation value is less than the threshold value. If the second variable in does not reach the second number of repetitions (NO in step 80), the second variable m is incremented by the control device 2 (step 81), thereby increasing the number of the second plurality by a predetermined number. The predetermined number is, for example, 2. As a method of increasing the number of the second plurality, it is preferable to evenly increase the number of the second plurality at both ends of receiving openings. In the case of the scanning line No 31, the ultrasound transducers D10 and D52 adjacent to both ends of the first plurality of ultrasound transducers D11 to D51 are increased (step 82). A second ultrasound image is generated using the ultrasound echo signals output from an increased number of ultrasound transducers (steps 74 to 76). The processing of steps 82 and 74 to 76 are repeated until the evaluation value of the image of the insertion needle 40 extracted from the second ultrasound image becomes equal to or greater than the threshold value or the second variable m reaches the second number of repetitions. In this manner, the control device 2 (a second control device) repeats the processing for generating the second acoustic wave image and the evaluation value calculation processing while increasing the number of second plurality of ultrasound transducers until the evaluation value becomes equal to or greater than the threshold value. In a case where the number of repetitions indicated by the second variable in reaches the second number of repetitions (second number of times), the processing for generating the second acoustic wave image and the evaluation value calculation processing are stopped. The number by which the second plurality is increased is not limited to 2, and may be, for example, 4 or 6, and an even number is preferable.

In the processing procedure shown in FIGS. 3 and 4, the first plurality of ultrasound transducers are D11 to D51, for example, in the case of the scanning line No 31, and the second plurality of ultrasound transducers are, for example, the ultrasound transducers D1 to D61 that are the maximum number of receiving openings. However, in the processing procedure shown in FIGS. 8 to 10, since the number of the second plurality is increased, the second plurality of ultrasound transducers before increasing the number cannot be ultrasound transducers (ultrasound transducers D1 to D61 in the case of the scanning line No 31) that are the maximum number of receiving openings. Therefore, in the processing procedure shown in FIGS. 8 to 10, the number of second ultrasound transducers before increasing the number needs to be less than 61 ultrasound transducers. In addition, the number of second plurality of ultrasound transducers before increasing the number may be the same as the number of first plurality of ultrasound transducers.

In the above-described embodiment shown in FIGS. 8 to 10, in a case where an evaluation value calculation command is given, the image of the insertion needle 40 is extracted from the first ultrasound image, and the evaluation value is calculated. However, in a case where the evaluation value calculation command is given, the doctor may generate the second ultrasound image in a state in which the extraction of the image of the insertion needle 40 from the first ultrasound image and the calculation of the evaluation value are skipped, since the image of the insertion needle 40 is not clearly seen in the first ultrasound image.

In addition, in the above-described embodiment, in order to generate the second ultrasound image, ultrasound waves are transmitted again. However, in the case of generating the first ultrasound image, if all pieces of ultrasound echo data obtained by digitally converting all ultrasound echo signals received by ultrasound transducers are stored in the ultrasound echo data storage device 9, the second ultrasound image can be generated using the ultrasound echo data obtained by digitally converting the ultrasound echo signals of the second plurality of ultrasound transducers, among the stored pieces of ultrasound echo data, without transmitting ultrasound waves again.

What is claimed is:

1. An acoustic wave image generating apparatus, comprising:
    an acoustic wave probe in which a plurality of acoustic wave transducers are arranged in at least one direction;
    a controller configured to:
       drive the acoustic wave transducers to transmit acoustic waves from the acoustic wave transducers to a subject;
       generate a first acoustic wave image of the subject based on an acoustic wave echo from the subject using acoustic wave echo signals output from a first plurality of the acoustic wave transducers whose number is smaller than the total number of the plurality of acoustic wave transducers;
       calculate an evaluation value of discontinuity of a needle for a needle image included in the first acoustic wave image;
       generate a second acoustic wave image of the subject using acoustic wave echo signals output from a second plurality of the acoustic wave transducers, the number of which is larger than the number of first plurality of acoustic wave transducers, in a case where the evaluation value that is calculated is less than a threshold value regardless of a needle puncture angle; and
       display the first acoustic wave image on a display screen in a case where the evaluation value that is calculated is equal to or greater than the threshold value and display the second acoustic wave image on the display screen in a case where the evaluation value that is calculated is less than the threshold value.

2. The acoustic wave image generating apparatus according to claim 1,
    wherein the controller is further configured to extract the needle image from the first acoustic wave image, and
    wherein the controller is further configured to calculate the evaluation value of discontinuity of the needle for the needle image that is extracted.

3. The acoustic wave image generating apparatus according to claim 2,
    wherein the controller is further configured to repeat transmission of acoustic waves based on the driving, generate the first acoustic wave image, and extract the needle image in a case where the needle image is not extracted.

4. The acoustic wave image generating apparatus according to claim 3,
    wherein the controller is further configured to stop the transmission of acoustic waves based on the driving, generation of the first acoustic wave image, and the extraction of the needle image in a case where the number of repetitions reaches a first number of times or in a case where a stop command is given.

5. The acoustic wave image generating apparatus according to claim 1,
    wherein the controller is further configured to calculate the evaluation value of the discontinuity of the needle for the needle image included in the first acoustic wave image in a case where the first acoustic wave image is displayed and an evaluation value calculation command for starting calculation of the evaluation value is input.

6. The acoustic wave image generating apparatus according to claim 1,
    wherein the controller is further configured to repeat processing for increasing the number of second plurality of acoustic wave transducers by a predetermined number, processing for generating the second acoustic wave image of the subject using acoustic wave echo signals output from the second plurality of acoustic wave transducers increased by the predetermined number, and processing for calculating the evaluation value of discontinuity of the needle using the generated second acoustic wave image, until the evaluation value becomes equal to or greater than the threshold value in a case where the evaluation value that is calculated is less than the threshold value.

7. The acoustic wave image generating apparatus according to claim 6,
    wherein, in a case where the number of repetitions reaches a second number of times, the controller stops calculating the evaluation value and generating the second acoustic wave image of the subject.

8. The acoustic wave image generating apparatus according to claim 1,
    wherein the first plurality of acoustic wave transducers and the second plurality of acoustic wave transducers overlap each other, and the acoustic wave transducer present at a center of the first plurality of acoustic wave transducers and the acoustic wave transducer present at a center of the second plurality of acoustic wave transducers are the same.

9. The acoustic wave image generating apparatus according to claim 8,
    wherein both the first plurality and the second plurality are odd numbers.

10. A control method of an acoustic wave image generating apparatus, comprising:
    causing driving of acoustic wave transducers of an acoustic wave probe, in which a plurality of acoustic wave transducers are arranged in at least one direction, to transmit acoustic waves from the acoustic wave transducers to a subject;
    causing generation of a first acoustic wave image of the subject based on an acoustic wave echo from the subject using acoustic wave echo signals output from a first plurality of the acoustic wave transducers whose number is smaller than the total number of the plurality of acoustic wave transducers;
    causing calculation of an evaluation value of discontinuity of a needle for a needle image included in the first acoustic wave image;

causing generation of a second acoustic wave image of the subject using acoustic wave echo signals output from a second plurality of the acoustic wave transducers, the number of which is larger than the number of first plurality of acoustic wave transducers, in a case where the evaluation value that is calculated is less than a threshold value regardless of a needle puncture angle; and causing display of the first acoustic wave image on a display screen in a case where the evaluation value that is calculated is equal to or greater than the threshold value and display of the second acoustic wave image on the display screen in a case where the evaluation value that is calculated is less than the threshold value.

* * * * *